(12) United States Patent
Lopez et al.

(10) Patent No.: US 8,234,074 B2
(45) Date of Patent: Jul. 31, 2012

(54) METHODS, SYSTEMS, AND COMPUTER PROGRAM PRODUCTS FOR SIMULATING BIOMEMBRANCES USING COARSE GRAIN MODELS

(75) Inventors: Carlos F. Lopez, Philadephia, PA (US); Steven O. Nielsen, Philadelphia, PA (US); Preston B. Moore, Philadelphia, PA (US); Michael L. Klein, Ocean City, NJ (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 705 days.

(21) Appl. No.: 10/459,698

(22) Filed: Jun. 12, 2003

(65) Prior Publication Data
US 2004/0102941 A1 May 27, 2004

Related U.S. Application Data

(60) Provisional application No. 60/388,527, filed on Jun. 13, 2002.

(51) Int. Cl.
*G01N 33/50* (2006.01)
*G01N 33/48* (2006.01)

(52) U.S. Cl. .......................................... 702/19; 702/20

(58) Field of Classification Search .......................... None
See application file for complete search history.

(56) References Cited

U.S. PATENT DOCUMENTS

| 6,019,998 | A | 2/2000 | Nomoto et al. |
| 6,541,071 | B1 | 4/2003 | Bookbinder et al. |
| 2004/0107056 | A1 | 6/2004 | Doerksen et al. |
| 2004/0215400 | A1 | 10/2004 | Slovic et al. |

OTHER PUBLICATIONS

Saiz et al. (2002). Towards an Understanding of Complex Biological Membranes from Atomistic Molecular Dynamics Simulations. Bioscience Reports, 22, 151-173.*
Lopez et al. (2002). Computer Simulation Studies of biomembranes using a coarse grain model. Computer Physics Communications. Clarification of publication date obtained from science direct website on Jun. 6, 2006.*
Chiu et al., Combined Monte Carlo and Molecular Dynamics Simulation of Hydrated Lipid-Cholesterol Lipid Bilayers at Low Cholesterol Concentration, Mar. 2001, Biophysical Journal, vol. 80, pp. 1104-1114.*
Bandyopadhyay, S. et al., "Molecular Dynamics Study of the Effect of Surfactant on a Biomembrane," *J. Phys. Chem. B*, vol. 105, pp. 5979-5986 (2001).
Kim, D. and Klein, L., "Liquid Hydrogen Fluoride with an Excess Proton: Ab Initio Molecular Dynamics Study of a Superacid," *J. Am. Chem. Soc.*, vol. 121, pp. 1121-11252 (1999).
Klein, M.L., "Water on the Move," *Science*, vol. 291, pp. 2106-2107 (Mar. 16, 2001).
Lopez, C.F. et al., "Computer simulation studies of biomembranes using a coarse grain model," *Computer Physics Communications*, vol. 147, pp. 1-6 (2002).
Lopez, C.F. et al., "Self-assembly of a phospholipid Langmuir monolayer using coarse-grained molecular dynamics simulations," *J. Phys.: Condens. Matter*, vol. 14, pp. 9431-9444 (2002).
MRSEC Overview, 3 pages, from http://www.lrsm.upenn.edu/lrsm/mrseclrsm.html, (last modified Jan. 2001)).
Nielsen, S.O. and Klein, M.L., "A Coarse Grain Model for Lipid Monolayer and Bilayer Studies," in Nielaba, P. et al. (Eds.), *Bridging Time Scales: Molecular Simulations for the Next Decade*, Springer, ISBN No. 3-540-44317-7, pp. 27-63 (2002).
Saitta, A.M. and Klein, M.L., "First-Principles Molecular Dynamics Study of the Rupture Processes of a Bulklike Polyethylene Knot," *J. Phys. Chem. B*, vol. 105, pp. 6495-6499 (2001).
Saitta, A.M. et al., "Influence of a knot on the strength of a polymer strand," *Nature*, vol. 399, pp. 46-48 (May 6, 1999).
Saiz, L. and Klein, M., "Influence of Highly Polyunsaturated Lipid Acyl Chains of Biomembranes on the NMR Order Parameters," *J. Am. Chem. Soc.*, vol. 123, pp. 7381-7387 (2001).
Saiz, L. and Klein, M.L., "Structural Properties of a Highly Polyunsaturated Lipid Bilayer from Molecular Dynamics Simulations," *Biophysical Journal*, vol. 81, pp. 204-216 (Jul. 2001).
Shelley, J.C. et al., "A Coarse Grain Model for Phospholipid Simulations," *J. Phys. Chem. B*, vol. 105, pp. 4446-4470 (2001).
Shelley, J.C. et al., "Simulations of Phospholipids Using a Coarse Grain Model," *J. Phys. Chem. B*, vol. 105, pp. 9785-9792 (2001).
Yarne, D. A. et al., "Structural and dynamical behavior of an azide anion in water from ab initio molecular dynamics calculations," *Chemical Physics*, vol. 28, pp. 163-169 (2000).
International Search Report from PCT Application No. PCT/US03/18220, filed Jun. 12, 2003, 4 pages (mailed Sep. 22, 2003).
Frenkel, D. and Smit, B., *Understanding Molecular Simulation: From Algorithms to Applications*, Academic Press, San Diego, CA, pp. 19-147 and 387-394 (1996).
Nielsen, S.O., et al., "Coarse Grain Models and the Computer Simulation of Soft Materials," *J. Phys.: Condens. Matter* 16:R481-R512, IOP Publishing (Apr. 2004).
Supplementary European Search Report for European Patent Application No. EP 03 73 4514, European Patent Office, Munich, Germany, completed Jul. 6, 2005.
Frenkel, D. and Smit, B., *Understanding Molecular Simulation From Algorithms to Applications*, Second Edition, Academic Publishers, ISBN No. 0-12-267351-4, entire book submitted (2002).

(Continued)

*Primary Examiner* — Jason Sims
(74) *Attorney, Agent, or Firm* — Sterne, Kessler, Goldstein & Fox P.L.L.C.

(57) ABSTRACT

A coarse grain model that mimics a lipid molecule, such as dimyristoylphosphatidylcholine (DMPC), is used to simulate self-assembly of a lamellar bilayer starting from a disordered configuration. The coarse grain model is orders of magnitude less demanding of CPU time compared to all-atom models. An initial bilayer-like structure is generated from a disordered configuration of the coarse grain models using a Monte Carlo simulation. The initial bilayer-like structure is refined using a molecular dynamics simulation. For relatively small systems, the molecular dynamics simulation can be performed under constant volume or constant pressure conditions. For larger systems, the molecular dynamics simulation is preferably performed under constant pressure conditions.

12 Claims, 7 Drawing Sheets

OTHER PUBLICATIONS

Goetz, R. and Lipowsky, R., "Computer simulations of bilayer membranes: Self-assembly and interfacial tension," *Journal of Chemical Physics*, vol. 108, No. 17, Published by The American Institute of Physics, pp. 7397-7409 (May 1, 1998).

Goetz, R. et al., "Mobility and Elasticity of Self-Assembled Membranes," *Physical Review Letters*, vol. 82, No. 1, Published by The American Physical Society, pp. 221-224 (Jan. 4, 1999).

Lindahl, E. and Edholm, O., "Mesoscopic Undulations and Thickness Fluctuations in Lipid Bilayers from Molecular Dynamics Simulations," *Biophysical Journal*, vol. 79, No. 1, Published by The Biophysical Society, pp. 426-433 (Jul. 2000).

Moore, P.B. et al., "Dynamical Properties of a Hydrated Lipid Bilayer from a Multinanosecond Molecular Dynamics Simulation," *Biophysical Journal*, vol. 81, No. 5, Published by The Biophysical Society, pp. 2484-2494 (Nov. 2001).

Shelley, J.C. et al., "Simulations of Phospholipids Using a Coarse Grain Model," *Journal of Physical Chemistry B*, vol. 105, No. 40, Published by The American Chemical Society, pp. 9785-9792 (Oct. 11, 2001).

Tuckerman, M.E. and Martyna, G.J., "Understanding Modern Molecular Dynamics: Techniques and Applications," *Journal of Physical Chemistry B*, vol. 104, No. 1, Published by The American Chemical Society, pp. 159-178 (Jan. 13, 2000).

Venturoli, M. and Smit, B., "Simulating the self-assembly of model membranes," *PhysChemComm*, 5 pages (1999).

Weikl, T. R. et al., "Unbinding transitions and phase separation of multicomponent membranes," *Physical Review E*, vol. 62, No. 1, Published by The American Physical Society, pp. R45-R48 (Jul. 2000).

Wilson, M.W. et al., "Replicated Data and Domain Decomposition Molecular Dynamics Techniques for Simulation of Anisotropic Potentials," *Journal of Computational Chemistry*, vol. 18, No. 4, Published by John Wiley & Sons, pp. 478-448 (1997).

\* cited by examiner

METHODS, SYSTEMS, AND COMPUTER PROGRAM PRODUCTS FOR SIMULATING BIOMEMBRANCES USING COARSE GRAIN MODELS

CROSS-REFERENCE TO RELATED APPLICATIONS

This application claims the benefit of U.S. Provisional Application Ser. No. 60/388,527, filed on Jun. 13, 2002, which is incorporated herein by reference in its entirety.

STATEMENT REGARDING FEDERALLY-SPONSORED RESEARCH

This invention was made with government support under Grant No. DMR00-79909 awarded by the National Science Foundation. The U.S. Government has certain rights in this invention.

BACKGROUND OF THE INVENTION

1. Field of the Invention

The present invention relates generally to in-silico molecular processing and, more particularly, to methods, systems, and computer program products for simulating biomembranes using coarse grain models.

2. Related Art

Many processes in biology, including membrane fusion membrane-protein interactions, and oxidative phosphorylation, take place at the membrane level. The idea of micron size (μm) domain formation in membranes ('rafts') has been invoked to explain mechanisms where lateral lipid organization plays an important role. A broader understanding of the lipid interactions at a mesoscopic level is therefore desired.

Atomic simulation techniques have developed to the point that it is possible to model phospholipid membranes relatively accurately. Unfortunately, conventional algorithms and computer power limit such studies to domain sizes of 5-10 nm and time scales of approximately 10 ns. Thus, much of the collective phenomena described above is computationally unattainable.

What is needed, therefore are methods, systems, and computer program products for studying phospholipid bilayer behavior that are faster than conventional techniques and/or that can study greater time scales than conventional techniques.

SUMMARY OF THE INVENTION

The present invention is directed to methods, systems, and computer program products for studying phospholipid bilayer behavior using coarse grain models. The present invention allows coarse grain models to be used to extend not only the size of the bilayer system under study, but also the effective time scale probed in simulations.

In accordance with the present invention, a coarse grain model designed to mimic a lipid molecule, such as dimyristoylphosphatidylcholine (DMPC), is used to simulate self-assembly of a lamellar bilayer starting from a disordered configuration. The coarse grain model is orders of magnitude less demanding of CPU time compared to all-atom models. An initial bilayer-like structure is generated from a disordered configuration of the coarse grain models using a Monte Carlo simulation. The initial bilayer-like structure is refined using a molecular dynamics simulation. For relatively small systems, the molecular dynamics simulation can be performed under constant volume conditions. For larger systems, the molecular dynamics is performed under constant pressure conditions.

Additional features and advantages of the invention will be set forth in the description that follows. Yet further features and advantages will be apparent to a person skilled in the art based on the description set forth herein or may be learned by practice of the invention. The advantages of the invention will be realized and attained by the structure particularly pointed out in the written description and claims hereof as well as the appended drawings.

It is to be understood that both the foregoing summary and the following detailed description are exemplary and explanatory and are intended to provide further explanation of the invention as claimed.

BRIEF DESCRIPTION OF THE DRAWINGS/FIGURES

The present invention will be described with reference to the accompanying drawings, wherein like reference numbers indicate identical or functionally similar elements. Also, the leftmost digit(s) of the reference numbers identify the drawings in which the associated elements are first introduced.

DETAILED DESCRIPTION OF THE INVENTION

I. Introduction

Figure 1:
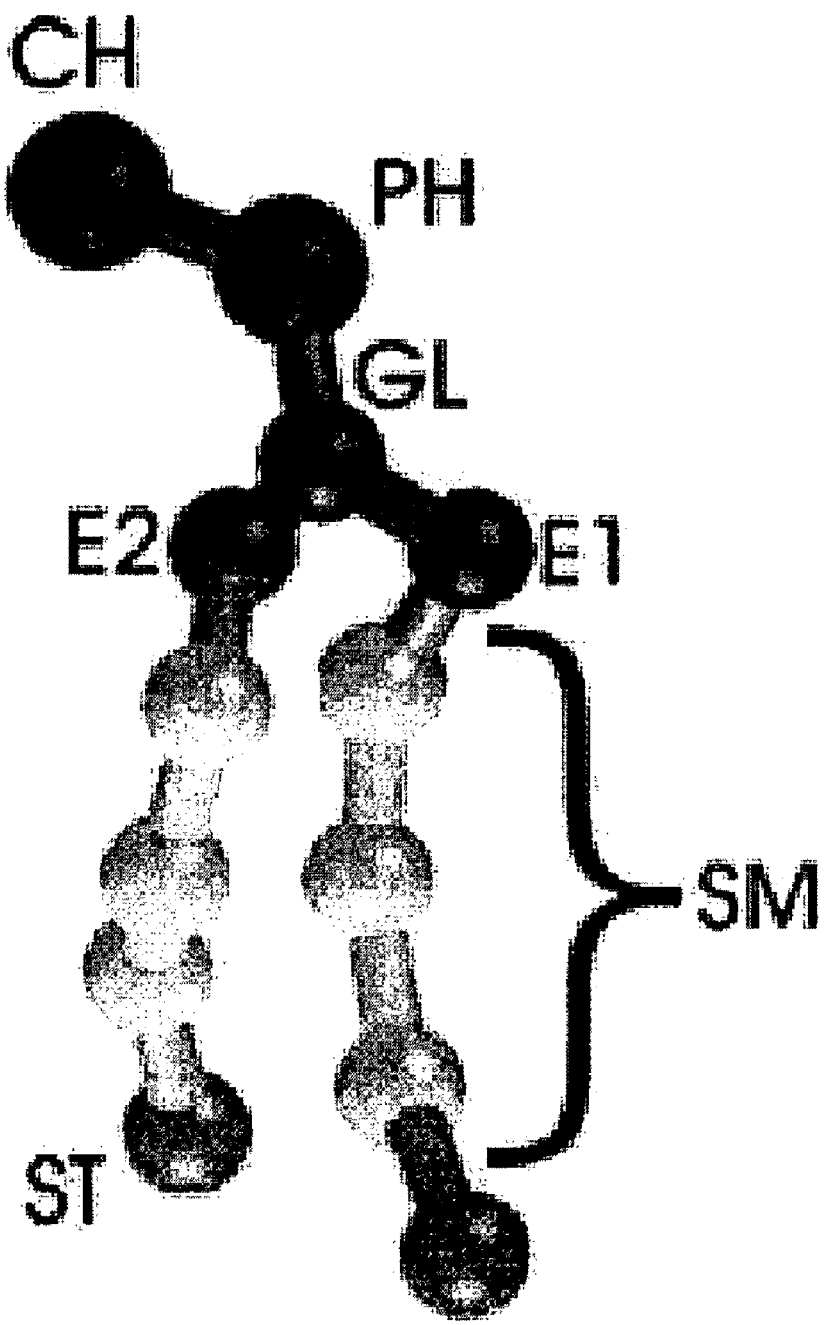
FIG. 1 illustrates a coarse grain ("CG") model for dimyristoyl-sn-glycero-phosphatidylcholine (DMPC).

Atomic simulation techniques suffer from computational limitations because of the number and complexity of features and factors to be analyzed. In accordance with the present invention, simulations are performed using coarse grain (CG) models, which use substantially less computer time than atomic simulations. See, for example:

R. Goetz, T. Lipowski, J. Chem. Phys. 108 (1998) 7397;

T. R. Weikl, R. R. Netz, R. Lipowsky, Phys. Rev. E 62 (2000) R45;

R. Goetz, G. Gompper, R. Lipowsky, Phys. Rev. Lett. 82 (2000) 221; and

M. Venturoli, B. Smit, Phys. Chem. Comm. 10 (1999); all of which are incorporated herein by reference in their entireties.

The present invention is directed to methods, systems, and computer program products for studying phospholipid bilayer behavior using coarse grain models. The present invention allows CG models to be used to extend not only the size of the bilayer system under study, but also the effective time scale probed in simulations.

Simulation of the formation of the bilayer-like structure can be performed under constant volume and/or constant pressure conditions. Constant volume simulations generally require a prior knowledge of the volume of the resultant bilayer-like structure. A prior knowledge of the volume of the resultant bilayer-like structure is generally determinable for relatively simple structures. For larger and/or more complex structures, however, the volume of the resultant bilayer-like structure can be difficult to know or determine in advance. In such situations, and others, simulations are performed under constant pressure conditions, which do not require a prior knowledge of the volume of the resultant bilayer-like structure.

The present invention is described herein using a coarse grain ("CG") model of dimyristoyl-sn-glycero-phosphatidyl-choline (DMPC), a common membrane lipid. See, for example:

J. C. Shelley, M. Y. Shelly, R. C. Reeder, S. Bandyopadhyay, M. L. Klein, J. Phys. Chem. B 105 (2001) 4464-4470;

J. C. Shelley, M. Y. Shelly, R. C. Reeder, S. P. Bandyopadhyay, P. B. Moore, M. L. Klein, J. Chem. Phys. (2001); (together referred to as the "CGD-MPC papers"), all of which are incorporated by reference in their entireties.

The present invention is not, however, limited to use with the CG model of DMPC. Based on the teachings herein, one skilled in the relevant art(s) will understand that the present invention is applicable to CG models of other membrane lipids as well.

A CG model for phospholipids, which semi-quantitatively reproduces the density profile of an aqueous DMPC bilayer has been developed. See, for example, the CG-DMPC papers, discussed above. The model is useful for simulating self-assembly of a DMPC bilayer from a thoroughly mixed initial state. The CG model is also useful for simulating the formation of a reverse columnar phase in a system composed of phospholipids, alkanes and water.

A CG model in accordance with the present invention is sufficiently accurate to study a range of phenomena at a level of efficiency that is roughly four orders of magnitude faster than atomistic models. A CG model in accordance with the present invention can be used to imitate a wide range of phenomena in phospholipid systems such as the self-assembly of systems containing multiple bilayers to elucidate bilayer roughness, lateral partitioning of phospholipids, and membrane fusion. For surfactant system models, see the CG-DMPC papers, discussed above. The present invention can be used to compliment studies of a range of biological phenomena addressable by MD simulations.

II. Coarse Grain Model

FIG. 1 illustrates a CG model 100 for DMPC. The CG model 100 uses simplified representations for water, alkanes and phospholipids. A model for each type of molecule mimics physical and/or structural features known from experimental and/or atomistic simulations. See S. Bandyopadhyay, J. C. Shelley, M. L. Klein, J. Phys. Chem. B 105 (2001) 5979-5986, incorporated herein by reference in its entirety. The model and its development are described in the CG-DMPC papers, discussed above.

In FIG. 1, single spherical sites represent triplets of carbon atoms in hydrocarbons and their accompanying hydrogen atoms. The hydrocarbon sites are linked together to form chains using stretching and bending potentials. Single spherical sites also represent triplets of water molecules.

Single spherically symmetric sites are used to represent the choline (CH), phosphate (PH), glycerol backbone (GL, namely $CH_2$—CH—$CH_2$), and ester groups ($^-O_2CCH_2$, E1 and E2) of DMPC. The lipid tails of DMPC were modeled using the alkane model described above and are labeled SM for the $(CH_2)_3$ sphere representations and ST for the $(CH_2)_2$ $CH_3$ sphere representations. The CH and PH groups carried charges of +e and −e, respectively, and a dielectric constant of 78 was used. 'Tinfoil' Ewald periodic boundary conditions were used to treat the electrostatic interactions. The DMPC model 100 semi-quantitatively reproduces structural aspects of the lipid. See the CG-DMPC papers, and S. Bandyopadhyay, J. C. Shelley, M. L. Klein, J. Phys. Chem. B 105 (2001) 5979-5986, which are discussed above.

III. Self-Assembly of a Bilayer

A simulation of the self-assembly of a system containing 548 W sites and 64 DMPC molecules at 303.15 K into a bilayer structure was carried out in a constant temperature and volume ensemble (NVT). The first part of the study was conducted using a Monte Carlo (MC) simulation. See the CG-DMPC papers, discussed above, for a description of the MC simulation.

Figure 2A:
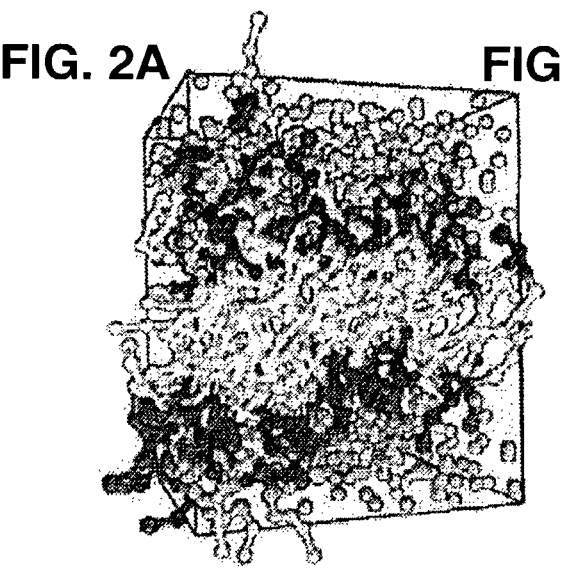
FIG. 2A illustrates a beginning configuration of the CG-DMPC self-assembly.

Referring to FIG. 2A, after the MC part of the study, the CG model of DMPC self-assembles into a bilayer-like structure 200. In FIG. 2A, water is depicted in light gray, head groups are depicted in medium-dark gray, and the tails of the lipid are in the center of the figure in light gray. As can be seen from FIG. 2A, several defects remain. For example, some phospholipid head groups remain in the core of the bilayer, and four hydrocarbon chains from DMPC molecules extend outside the bilayer. FIG. 2A is referred to herein as a beginning configuration of the CG-DMPC self-assembly.

Next, a molecular dynamic ("MD") simulation is performed, starting from the final configuration of the MC run illustrated in FIG. 2A. The MD simulation was conducted in the canonical ensemble using Nosé-Hoover chains of length 4. See, for example, D. Frenkel, B. Smit, "Understanding Molecular Simulation," Academic Press, San Diego, 1996; and M. E. Tuckerman, G. J. Matyna, J. Phys. Chem. B. 104 (2000) 159; which are incorporated herein by reference in their entireties. Multiple time step molecular dynamics were implemented using a three stage RESPA integration of the equations of motion. See D. Frenkel, B. Smit, "Understanding Molecular Simulation," Academic Press, San Diego, 1996, discussed above. The shortest steps, 1 fs, were used for bond-length and angle integration while the intermediate length steps, 2 fs, were used for non-bonded interactions less than 11 Å, and the long steps, 40 fs, were used for non-bonded interactions between 11 Å and the cut-off. The cut-off for the van der Waals potentials was set at 15 Å while that for the real-space part of the Ewald calculations was 22.9 Å. The simulation used an orthorhombic of cell dimensions 46.0 Å×45.3 Å×59.3 Å, and was run for 1 ns with a time step of 20 fs. Trajectory snapshots were collected every 50 steps for analysis.

Figure 2B:
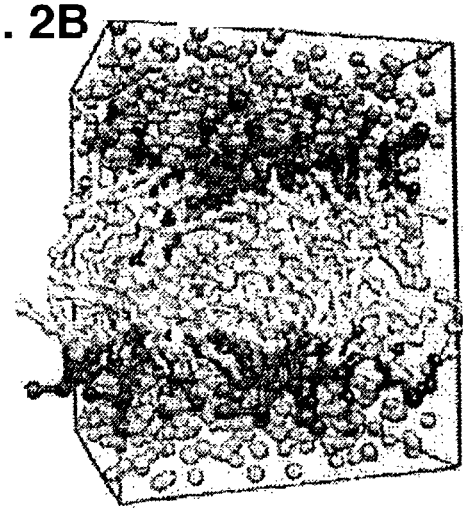
FIG. 2B illustrates a final configuration of the CG-DMPC self-assembly.

Within 500 psec, substantially all of the defects of FIG. 2A healed and a substantially defect-free bilayer resulted, as illustrated in FIG. 2B. FIG. 2B is referred to herein as a final configuration of the CG-DMPC self-assembly. In FIG. 2B, as with FIG. 2A, water is depicted in light gray, head groups are depicted in medium-dark gray, and the tails of the lipid are in the center of the figure in light gray.

Self-assembly using MD simulations is relatively fast. This is likely because the soft, smoothed potentials eliminate many local minima in the potential energy surface, fewer independent interaction sites encourage collective motion, and the simulation system is still relatively small, providing a feedback mechanism for self-assembly.

V. Lipid diffusion Under Constant Pressure Conditions

The above-described techniques for studying phospholipid bilayer behavior are performed under constant volume conditions, which requires a prior knowledge of the volume of the resultant bilayer-like structure. A prior knowledge of the volume of the resultant bilayer-like structure is generally determinable for relatively simple structures. For larger and/or more complex structures, however, the volume of the resultant bilayer-like structure can be difficult to know or determine in advance.

Figure 3:
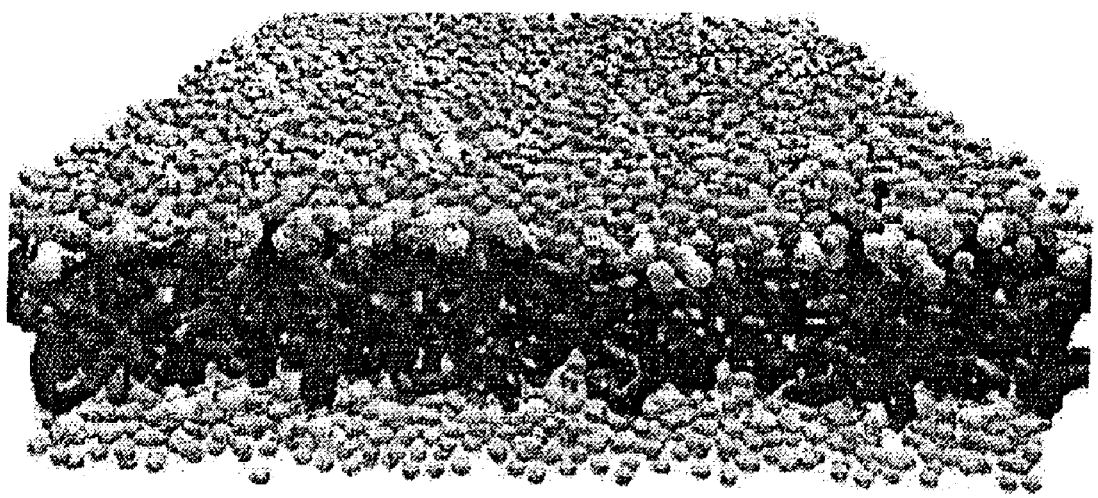
FIG. 3 illustrates a 1024 CG-DMPC bilayer system.

In accordance with the present invention, for larger simulations, MD simulations are performed using constant pressure conditions. For example, MD simulations were performed for a larger simulation with 1024 CG-DMPC molecules and 8768 W sites. The simulation was run in the constant pressure and temperature (NPT) ensemble for 1 ns with a 20 fs time step and an orthorhombic cell. The choice of Nosé-Hoover chains for thermostats was the same as in the previously described 64 DMPC simulation. In addition, the pressure was controlled by four barostats. The average cell size was 180 Å×198 Å×56 Å. A snapshot of the system is shown in FIG. 3.

V. Structure of the Simulation

In order to examine the robustness of the invention, the simulation was compared with a previous simulation of a hydrated all-atom (AA) DMPC lipid bilayer. See P. B. Moore, D. F. Lopez, M. L. Klein, Biophys. J. 81 (2001) 2484, incorporated herein by reference in its entirety. This simulation included 64 DMPC lipid molecules and 1792 water molecules. The simulation was run for 10 ns in the constant energy and volume (NVE) ensemble. Details of the simulation can be found in M. R. Wilson, W. P. Allen, M. A. Warren, S. Sauron, W. Smith, J. Comp. Chem. 18 (1997) 478, incorporated herein by reference in its entirety.

Figure 4:
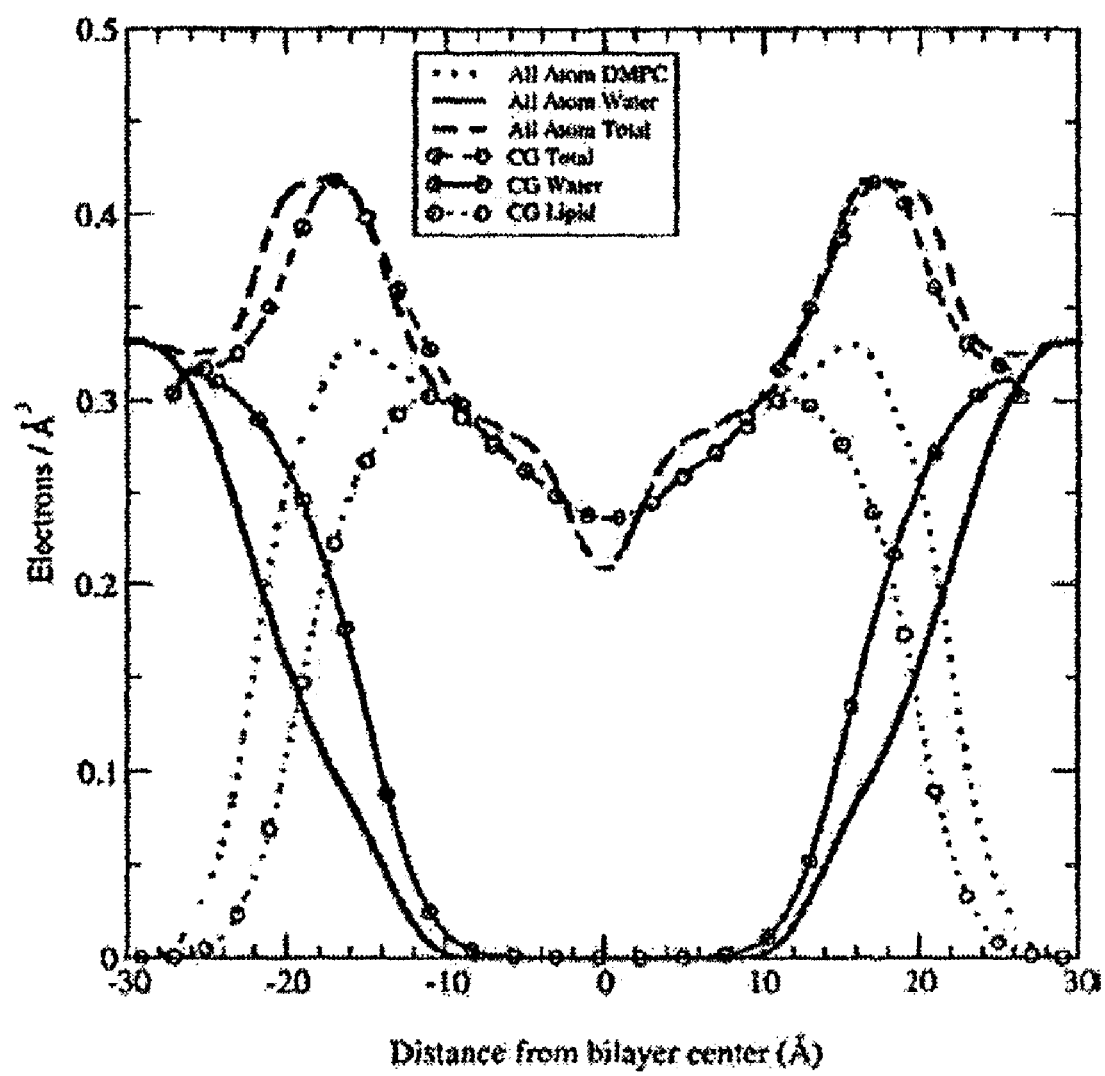
FIG. 4 illustrates a comparison of electron density profiles for all-atom and CG-DMPC simulations.

A value that is useful when comparing structural properties of membranes is the electron density profile normal to the bilayer surface, which can be obtained from X-ray experiments. A comparison of the electron density profile of AA-DMPC and CG-DMPC is shown in FIG. 4. The first feature apparent from the electron density profile is that the CG-DMPC head-group-to-head-group distance (d-spacing) is shorter than that of the AA simulation. The d-spacing for the AA simulation is 36 Å while the area per head group is 58 Å 2. In the CG study described herein, a d-spacing of 32 Å and an area per head group of 70 Å 2 was attained.

These values are in fair agreement with the AA values and show that a CG description of the lipid and a reduced number of sites can provide qualitatively similar results to those obtained from AA simulations. Although fine details of the AA lipid simulations may not be captured using CG models, the results are useful enough to warrant using this more phenomenological approach to study larger scale phenomena.

VI. Diffusion of the Lipid

The present invention permits investigation of larger systems and at longer time scales as compared to conventional techniques. With conventional all-atom simulations, even with the fastest algorithms it is relatively difficult to access time scales of more than 10 ns with a total system size of about 20,000 atoms. Other simulations have attempted to investigate longer simulations and larger systems but some simplifications in the electrostatics calculations were necessary to make the problem computationally tractable. See E. Lindahl, O. Edholm, Biophys. J. 79 (2000) 426-433, incorporated herein by reference in its entirety. However, electrostatic interactions have been previously shown to contribute significantly to system properties. In the simulations described herein, electrostatic interactions are not cut off.

Due to the use of different potentials and numbers of sites in the CG model it is useful to get an idea of the effective time scale being explored. In order to explore time-scale differences, the diffusion coefficient from the previous AA lipid simulation is compared with the present CG model. The diffusion constant (D) is calculated by obtaining the limiting slope of the mean square displacement according to:

$$D = \lim_{t \to \infty} \frac{1}{4} \frac{d}{dt} \langle |r_i(t) - r_i(0)|^2 \rangle, \quad \text{Eqs. (1)}$$

where $r_i$ is the center of mass position of each lipid molecule at time t and D, the two-dimensional diffusion coefficient on the membrane surface.

Figure 5A:
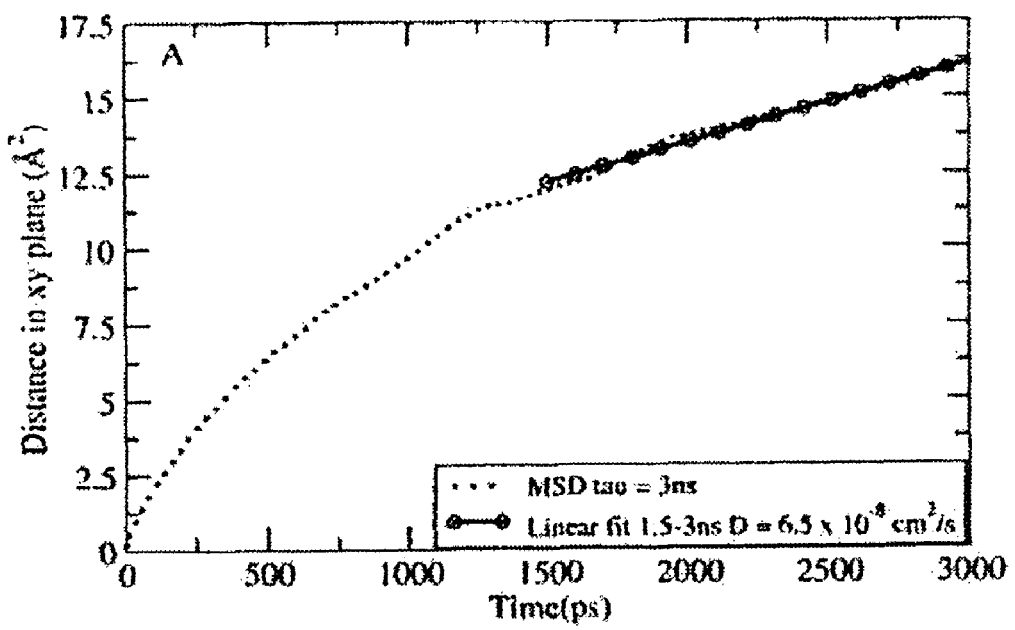
FIG. 5A illustrates a mean square displacement for all-atom DMPC, 10 ns total simulation time.
Figure 5B:
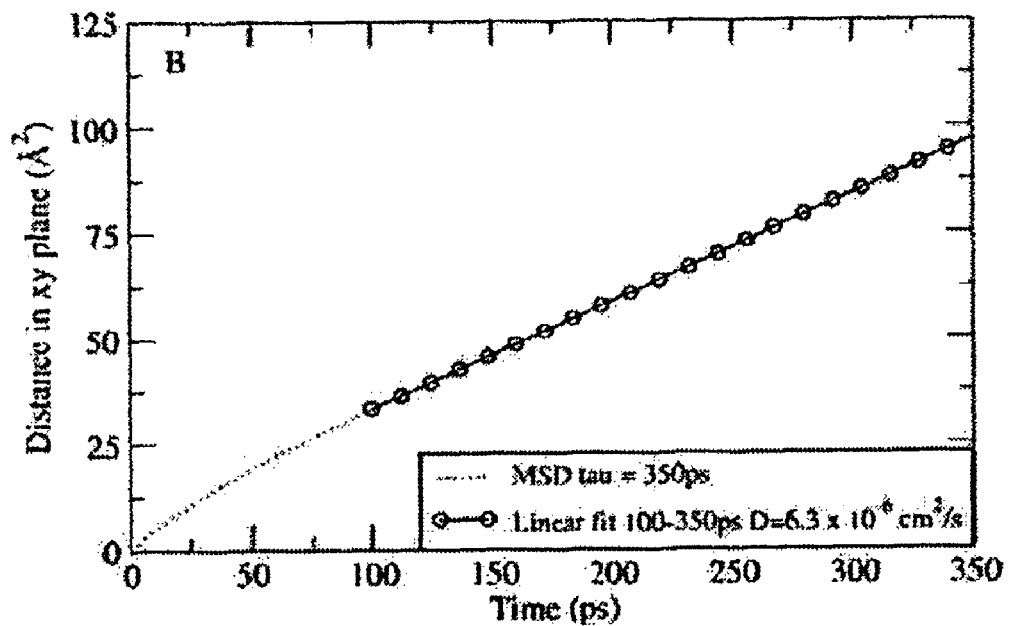
FIG. 5B illustrates a mean square displacement for CG-DMPC, 1 ns total simulation time.

FIGS. 5A and 5B illustrate a comparison of the results of the AA and CG models. FIG. 5A shows that the AA DMPC lipid molecules are still approaching the hydrodynamic limit while the molecules in FIG. 5B show a steady slope past 100 ps. The slopes yield $D_{AA}=6.5 \times 10^{-8}$ cm$^2$/s and $D_{CG}=6.3 \times 10^{-6}$ cm$^2$/s for the AA and CG models, respectively. This implies that the description of dynamic motions of the particles in the CG model is at least two orders of magnitude faster than that of the AA model. In addition, the reduced number of calculations from the forces (118 interacting sites for AA vs. 13 sites for the CG) reduces the calculation time by roughly another two orders of magnitude. Since the CG model also utilizes a larger time step, it should now be possible to access dynamical properties in a time scale that is four orders of magnitude more than those performed to date.

VII. Processing Considerations

A decrease in computation time can be achieved with parallel computing. Techniques that can be used include, without limitation, replicated data scheme with force decomposition, and domain decomposition ("DD"). See, M. R. Wilson, W. P. Allen, M. A. Warren, S. Sauron, W. Smith, J. Comp. Chem. 18 (1997) 478, discussed above.

The present invention has been implemented with the replicated data technique, which provides relatively good scaling per processor. See, M. R. Wilson, W. P. Allen, M. A. Warren, S. Sauron, W. Smith, J. Comp. Chem. 18 (1997) 478, discussed above. The replicated data technique is relatively easy to implement and is suitable for available computer resources.

Distributed memory machines, such as 'Beowulf' clusters, provide relatively good scaling. For example, for a $2 \times 10^4$ particle system, distributed memory systems provide relatively good scaling from 1 to 32 processors. Beyond that, however, inter-processor communication can reduce performance.

Code issues, such as time and size, should be considered. Time scale issues include force calculation and integration time step. Time-step calculation will generally improve with faster computers and more processors. Code improvements can be implemented to take advantage of parallel computers.

The code optionally includes parallel algorithms such as DD coupled with fast multiple methods ("FMM"). The DD of short-range forces (such as Lennard-Jones) has been shown to scale linearly with the number of processors, provided that there is sufficient memory and disk space. Simulations of $\sim 10^7$ particles or larger systems can be readily obtained when only short-range forces are included. The current implementations of Ewald (e.g., Particle Mesh Ewald ("PME")) can be difficult to code efficiently on parallel computers due to real space (r) and reciprocal space (k) inter-conversions. Alternatively, the code can include a FMM, which does not have the PME difficulties. Although the PME is faster than FMM for small systems (e.g., $2 \times 10^4$ particles), larger systems will generally run faster with FMM. Thus, where lipid domains with $10^5$ or more particles are to be simulated, FMM is generally preferable. The FMM should be able to scale efficiently up to any amount of processors, provided that there is sufficient memory and processors.

An example implementation is now provided for a relatively large system of $10^5$ lipids. The code is implemented over 32 CPUs for 1000 lipids, which is $2 \times 10^4$ particles. In order to simulate a system with $10^5$ lipids ($\sim 10^6$ particles), FMM and DD are employed. The current time steps in the $2 \times 10^4$ particle simulations are on the order of 20 fs and take 90 s/step for one processor. Where access to 500 CPUs is possible, it is estimated that for the $\sim 10^5$ lipid system, assuming a factor of two in overhead, will execute in 36 s/step. In 1 month of computer time, this would result in 1 ns of simulation time. Taking into account the two order of magnitude increase in diffusion from the CG model, this would result in an effective time scale of 100 ns.

VIII. Process Flowchart

Figure 7:
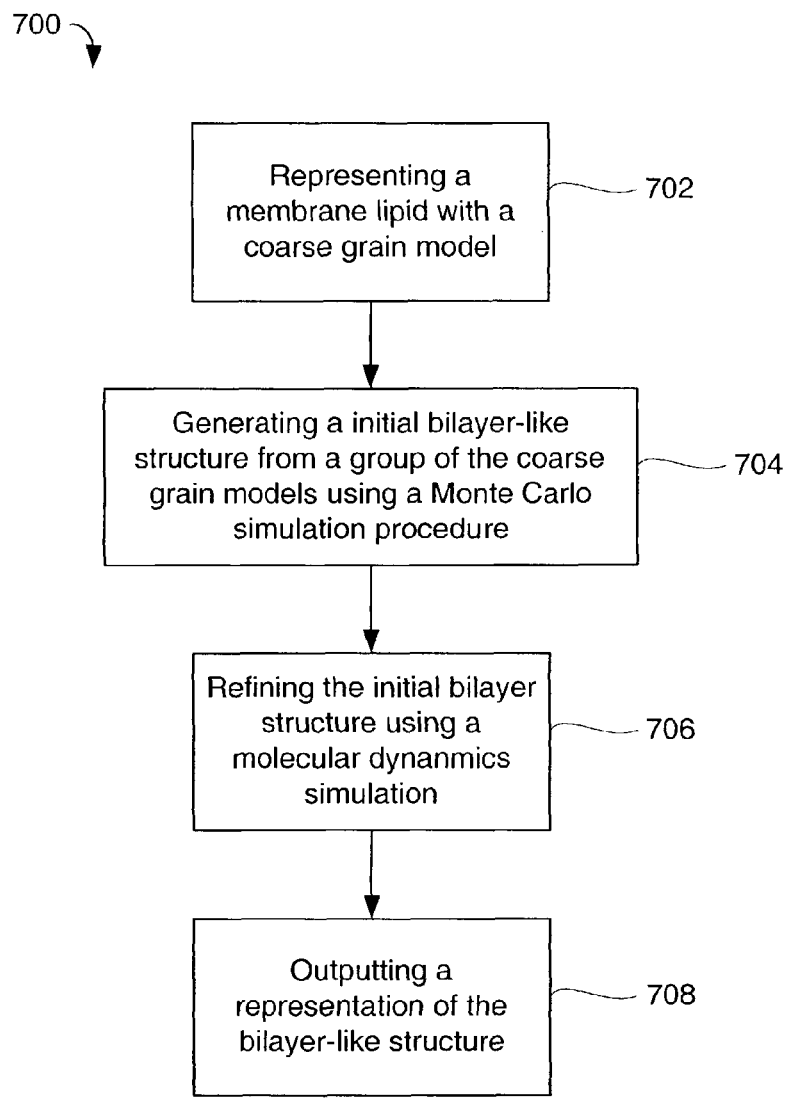
FIG. 7 is a process flowchart for implementing the present invention.

FIG. 7 is a process flowchart of an example method 700 for implementing the present invention. The process begins with step 702, which includes representing membrane lipid, such as a dimyristoyl-sn-glycero-phosphatidylcholine membrane lipid, with a coarse grain model.

Step 704 includes generating an initial bilayer-like structure from a group of the coarse grain models using a Monte Carlo simulation procedure. The group of coarse grain models can be a disordered group of coarse grain models.

Step 706 includes refining the initial bilayer structure using a molecular dynamics simulation. For larger systems, the molecular dynamics simulation is performed under constant pressure conditions. For smaller systems, the molecular dynamics simulation can be performed under constant pressure or constant volume conditions.

Step 708 includes outputting a representation of the refined bilayer-like structure. The refined bilayer-like structure can be used for, among other things, determining coarse grain force fields for the coarse grain model of the membrane lipid.

IX. Computer Program Product

The present invention can be implemented in one or more computer systems capable of carrying out the functionality described herein. For example, and without limitation, the process flowchart 700, or portions thereof, can be implemented in a computer system.

Figure 6:
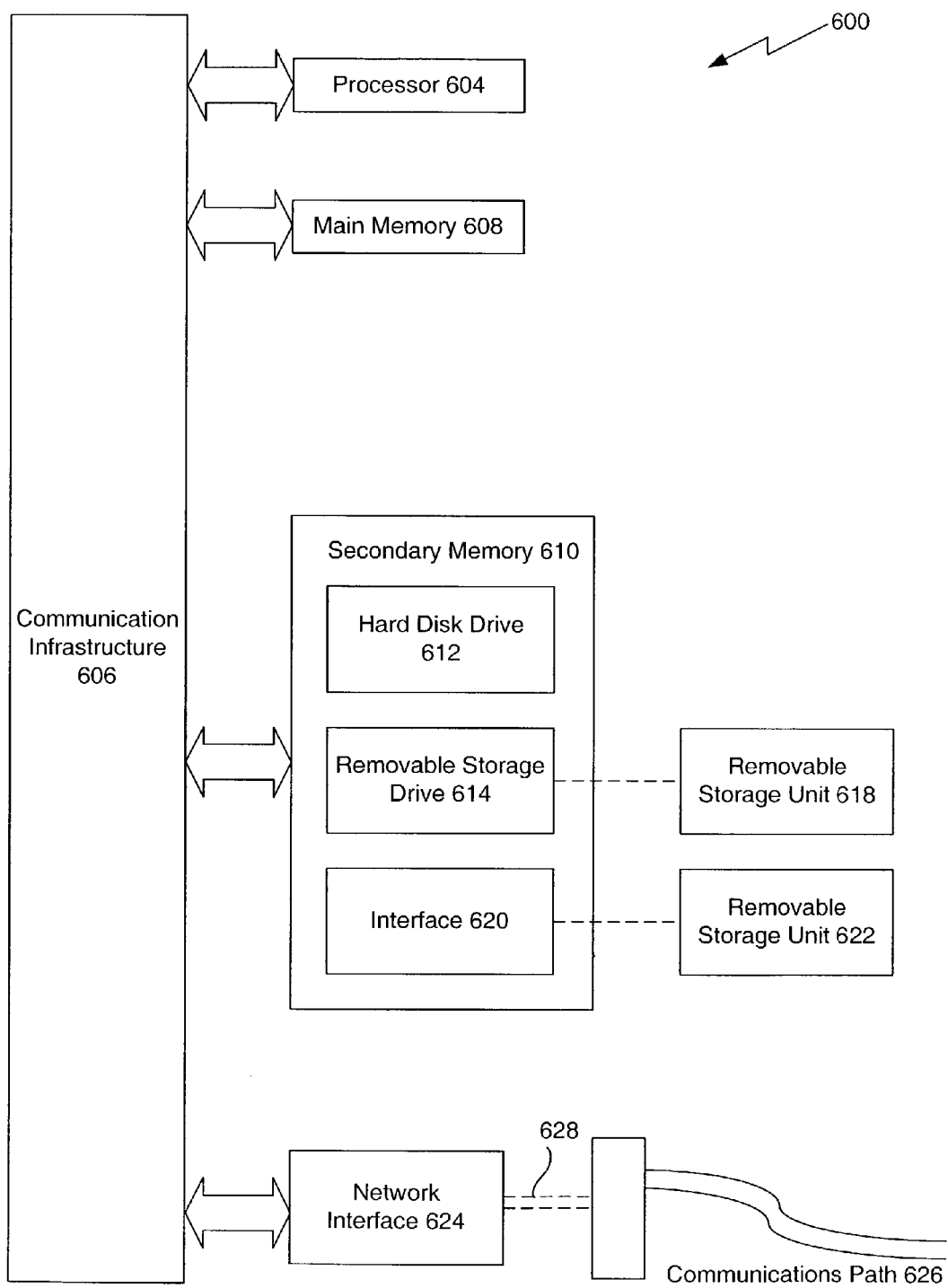
FIG. 6 is a block diagram of an example computer system for implementing the present invention.

FIG. 6 illustrates an example computer system 600. Various software embodiments are described in terms of this example computer system 600. After reading this description, it will be apparent to a person skilled in the relevant art(s) how to implement the invention using other computer systems and/or computer architectures.

The example computer system 600 includes one or more processors 604, coupled to a communication infrastructure 606.

Computer system 600 also includes a main memory 608, preferably random access memory (RAM).

Computer system 600 can also include a secondary memory 610, which can include, for example, a hard disk drive 612 and/or a removable storage drive 614, which can be a floppy disk drive, a magnetic tape drive, an optical disk drive, etc. Removable storage drive 614 reads from and/or writes to a removable storage unit 618 in a well known manner. Removable storage unit 618, represents a floppy disk, magnetic tape, optical disk, etc. which is read by and written to by removable storage drive 614. Removable storage unit 618 includes a computer usable storage medium having stored therein computer software and/or data.

In alternative embodiments, secondary memory 610 can include other devices that allow computer programs or other instructions to be loaded into computer system 600. Such devices can include, for example, a removable storage unit 622 and an interface 620. Examples of such can include a program cartridge and cartridge interface (such as that found in video game devices), a removable memory chip (such as an EPROM, or PROM) and associated socket, and other removable storage units 622 and interfaces 620 that allow software and data to be transferred from the removable storage unit 622 to computer system 600.

Computer system 600 can also include a communications interface 624, which allows software and data to be transferred between computer system 600 and external devices. Examples of communications interface 624 include, but are not limited to a modem, a network interface (such as an Ethernet card), a communications port, a PCMCIA slot and card, etc. Software and data transferred via communications interface 624 are in the form of signals 628, which can be electronic, electromagnetic, optical or other signals capable of being received by communications interface 624. These signals 628 are provided to communications interface 624 via a communications path 626. Communications path 626 carries signals 628 and can be implemented using wire or cable, fiber optics, a phone line, a cellular phone link, an RF link and other communications channels.

In this document, the terms "computer program medium" and "computer usable medium" are used to generally refer to media such as removable storage unit 618, a hard disk installed in hard disk drive 612, and signals 628. These computer program products are means for providing software to computer system 600.

Computer programs (also called computer control logic) are stored in main memory 608 and/or secondary memory 610. Computer programs can also be received via communications interface 624. Such computer programs, when executed, enable the computer system 600 to perform the features of the present invention as discussed herein. In particular, the computer programs, when executed, enable the processor(s) 604 to perform the features of the present invention. Accordingly, such computer programs represent controllers of the computer system 600.

In an embodiment where the invention is implemented using software, the software can be stored in a computer program product and loaded into computer system 600 using removable storage drive 614, hard disk drive 612 or communications interface 624. The control logic (software), when executed by the processor(s) 604, causes the processor(s) 604 to perform the functions of the invention as described herein.

In another embodiment, the invention is implemented primarily in hardware using, for example, hardware components such as application specific integrated circuits (ASICs). Implementation of the hardware state machine so as to perform the functions described herein will be apparent to persons skilled in the relevant art(s).

In yet another embodiment, the invention is implemented using a combination of both hardware and software.

X. Conclusion

The present invention has been described above with the aid of functional building blocks illustrating the performance of specified functions and relationships thereof. The boundaries of these functional building blocks have been arbitrarily defined herein for the convenience of the description. Alternate boundaries can be defined so long as the specified functions and relationships thereof are appropriately performed. Any such alternate boundaries are thus within the scope and spirit of the claimed invention. One skilled in the art will recognize that these functional building blocks can be implemented by discrete components, application specific integrated circuits, processors executing appropriate software and the like and combinations thereof.

While various embodiments of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents.

What is claimed is:

1. A method for simulating assembly of a membrane lipid bilayer with a coarse grain model of the membrane lipid, comprising:
    (1) representing the membrane lipid, with a coarse grain model;
    (2) generating an initial bilayer-like structure from a group of the coarse grain models using a Monte Carlo simulation procedure;
    (3) refining the initial bilayer-like structure using a molecular dynamics simulation to produce a substantially defect-free refined bilayer-like structure; and
    (4) outputting a representation of the refined substantially defect-free bilayer-like structure to a computer system,
    wherein each of (1)-(4) is performed on a suitably programmed computer,
    wherein the refined bilayer-like structure in (4) is substantially defect-free within 500 psec of simulation time when the method is performed on a model consisting of 548 W sites and 64 dimyristoyl-sn-glycero-phosphatidylcholine molecules run at 303.15 K in a constant temperature and volume ensemble, wherein each W site represents a triplet of water molecules, and wherein the coarse grain model results in an effective time scale of at least 100 ns.

2. The method according to claim 1, wherein (3) comprises performing the molecular dynamics simulation under constant pressure conditions.

3. The method according to claim 1, wherein (1) comprises representing a dimyristoyl-sn-glycero-phosphatidylcholine membrane lipid with a coarse grain model.

4. The method according to claim 1, wherein (3) comprises performing the molecular dynamics simulation under constant pressure and temperature conditions.

5. The method according to claim 3, wherein (1) further comprises representing the dimyristoyl-sn-glycero-phosphatidylcholine membrane lipid with at least 1000 coarse grain molecules and at least 5000 sites.

6. The method according to claim 5, wherein (3) comprises performing the molecular dynamics simulation under constant pressure conditions.

7. The method according to claim 3, wherein (1) comprises:
    (a) representing triplets of carbon atoms in hydrocarbons and their accompanying hydrogen atoms as spherical objects;
    (b) linking hydrocarbon sites together to form chains using stretching and bending potentials; and
    (c) representing triplets of water molecules as spherical objects.

8. The method according to claim 7, wherein (1) further comprises:
    (d) representing a choline backbone as a first spherical object;
    (e) representing a phosphate backbone as a second spherical object; and
    (f) representing a glycerol backbone as a third spherical object.

9. The method according to claim 1, wherein (2) comprises generating the initial bilayer-like structure from a disordered group of the coarse grain models.

10. The method according to claim 1, wherein (3) comprises conducting the molecular dynamics simulation in a canonical ensemble using Nosé-Hoover chain lengths of 4.

11. The method according to claim 1, wherein (3) comprises performing a multiple time step molecular dynamics simulation using a three stage RESPA integration of equations in motion.

12. The method according to claim 1, wherein (3) comprises:
    (a) conducting the molecular dynamics simulation in a canonical ensemble using Nosé-Hoover chain lengths of 4; and
    (b) performing a multiple time step molecular dynamics simulation using a three stage RESPA integration of equations in motion.

* * * * *